United States Patent
Odaibo et al.

(10) Patent No.: US 11,934,933 B2
(45) Date of Patent: *Mar. 19, 2024

(54) SYSTEMS AND METHODS USING WEIGHTED-ENSEMBLE SUPERVISED-LEARNING FOR AUTOMATIC DETECTION OF OPHTHALMIC DISEASE FROM IMAGES

(71) Applicants: Stephen Gbejule Odaibo, Houston, TX (US); David Gbodi Odaibo, Houston, TX (US)

(72) Inventors: Stephen Gbejule Odaibo, Houston, TX (US); David Gbodi Odaibo, Houston, TX (US)

(73) Assignee: Retina-Al Health, Inc., Houston, TX (US)

( * ) Notice: Subject to any disclaimer, the term of this patent is extended or adjusted under 35 U.S.C. 154(b) by 531 days.

This patent is subject to a terminal disclaimer.

(21) Appl. No.: 17/137,770

(22) Filed: Dec. 30, 2020

(65) Prior Publication Data

US 2021/0224594 A1 Jul. 22, 2021

Related U.S. Application Data

(63) Continuation of application No. 15/666,498, filed on Aug. 1, 2017, now Pat. No. 10,963,737.

(51) Int. Cl.
*G06N 20/20* (2019.01)
*A61B 3/00* (2006.01)
(Continued)

(52) U.S. Cl.
CPC .......... *G06N 20/20* (2019.01); *A61B 3/0025* (2013.01); *A61B 3/14* (2013.01); *A61B 5/7267* (2013.01);
(Continued)

(58) Field of Classification Search
CPC ........ G06N 20/20; G06N 3/044; G06N 3/045; G06N 20/00; G06N 3/082; G06N 3/084;
(Continued)

(56) References Cited

U.S. PATENT DOCUMENTS 8,820,931 B2 * 9/2014 Walsh .................. A61B 3/0025
351/208
2002/0186818 A1 * 12/2002 Arnaud .................. G06Q 30/02
378/165
(Continued)

*Primary Examiner* — Charlotte M Baker
(74) *Attorney, Agent, or Firm* — Elliott Law PLLC; Douglas H. Elliott; Nathan Q. Huynh

(57) ABSTRACT

Disclosed herein are systems, methods, and devices for classifying ophthalmic images according to disease type, state, and stage. The disclosed invention details systems, methods, and devices to perform the aforementioned classification based on weighted-linkage of an ensemble of machine learning models. In some parts, each model is trained on a training data set and tested on a test dataset. In other parts, the models are ranked based on classification performance, and model weights are assigned based on model rank. To classify an ophthalmic image, that image is presented to each model of the ensemble for classification, yielding a probabilistic classification score—of each model. Using the model weights, a weighted-average of the individual model-generated probabilistic scores is computed and used for the classification.

20 Claims, 12 Drawing Sheets

(51) Int. Cl.

| | | |
|---|---|---|
| *A61B 3/14* | (2006.01) | |
| *A61B 5/00* | (2006.01) | |
| *G06F 18/214* | (2023.01) | |
| *G06F 18/2413* | (2023.01) | |
| *G06F 18/25* | (2023.01) | |
| *G06N 3/044* | (2023.01) | |
| *G06N 3/045* | (2023.01) | |
| *G06N 20/00* | (2019.01) | |
| *G06V 10/44* | (2022.01) | |
| *G06V 10/764* | (2022.01) | |
| *G06V 10/80* | (2022.01) | |
| *G06V 10/82* | (2022.01) | |
| *G06V 40/18* | (2022.01) | |
| *G06V 40/19* | (2022.01) | |
| *G16H 30/40* | (2018.01) | |
| *G16H 50/20* | (2018.01) | |
| *G06N 3/082* | (2023.01) | |
| *G06N 3/084* | (2023.01) | |

(52) U.S. Cl.
CPC ........ *G06F 18/214* (2023.01); *G06F 18/2413* (2023.01); *G06F 18/254* (2023.01); *G06N 3/044* (2023.01); *G06N 3/045* (2023.01); *G06N 20/00* (2019.01); *G06V 10/454* (2022.01); *G06V 10/764* (2022.01); *G06V 10/809* (2022.01); *G06V 10/82* (2022.01); *G06V 40/19* (2022.01); *G06V 40/193* (2022.01); *G06V 40/197* (2022.01); *G16H 30/40* (2018.01); *G16H 50/20* (2018.01); *A61B 5/4842* (2013.01); *A61B 5/4878* (2013.01); *A61B 2576/02* (2013.01); *G06N 3/082* (2013.01); *G06N 3/084* (2013.01)

(58) Field of Classification Search
CPC ....... A61B 3/0025; A61B 3/14; A61B 5/7267; A61B 5/4842; A61B 5/4878; A61B 2576/02; G06F 18/214; G06F 18/2413; G06F 18/254; G06V 10/454; G06V 10/764; G06V 10/809; G06V 10/82; G06V 40/19; G06V 40/193; G06V 40/197; G16H 30/40; G16H 50/20
USPC ....................................................... 382/128
See application file for complete search history.

(56) References Cited

U.S. PATENT DOCUMENTS

| | | | | |
|---|---|---|---|---|
| 2010/0195050 A1* | 8/2010 | Sakagawa | ................ | A61B 3/12 351/208 |
| 2012/0274904 A1* | 11/2012 | Saito | ........................ | A61B 3/12 351/221 |
| 2012/0287401 A1* | 11/2012 | Bizios | .................. | A61B 3/0025 351/246 |
| 2012/0330140 A1* | 12/2012 | Yonezawa | ............ | A61B 3/1225 600/425 |
| 2015/0062590 A1* | 3/2015 | Bagherinia | ........ | G01B 9/02091 356/479 |
| 2015/0305614 A1* | 10/2015 | Narasimha-Iyer | .... | G06T 7/0012 351/206 |
| 2016/0007847 A1* | 1/2016 | Dziubak | .............. | A61B 3/1225 351/246 |
| 2016/0284103 A1* | 9/2016 | Huang | .................. | G01B 11/00 |

* cited by examiner

SYSTEMS AND METHODS USING WEIGHTED-ENSEMBLE SUPERVISED-LEARNING FOR AUTOMATIC DETECTION OF OPHTHALMIC DISEASE FROM IMAGES

PRIORITY INFORMATION

This application is a continuation of, and claims benefit to, pending U.S. Nonprovisional Application No. 15/666,498, filed on Aug. 1, 2017; and this application hereby incorporates herein U.S. Nonprovisional Application No. 15/666,498 as if set forth herein in its entirety.

FIELD OF THE INVENTION

The present invention relates to automated detection of ophthalmic diseases from images of the eye and its parts.

BACKGROUND OF THE INVENTION

The eye is the primary sensory organ involved in vision. There are a myriad of diseases which can affect the eye and result in visual deficit or blindness. Some of these diseases, such as diabetes, are systemic conditions which result in multiple organ dysfunction. Others of these diseases, such as age-related macular degeneration and primary open angle glaucoma, are primarily localized to the eyes. There is a significant and growing shortage of trained eye care providers competent to diagnose both primarily ophthalmic diseases and systemic diseases with ophthalmic manifestations. This shortage of expertise is an enormous burden on society, because errors and delays in diagnosis result in preventable morbidity and mortality. As a result of these factors, over the years there has been much interest in the development of computer-based systems that can automate the diagnosis of ophthalmic diseases.

A problem in the field of automatic detection of ophthalmic diseases is that most supervised-learning approaches employed to date have been based on explicit engineering of disease features. For example, in the case of diabetes the worker would explicitly write a program, for instance, specifying that any small roundish and red dot on the image is a retinal hemorrhage and is a marker for diabetic retinopathy. Such an explicit approach generalizes relatively poorly, and is not as powerful and accurate as end-to-end learning which detects important features automatically. End-to-end learning approaches are typically based on "big data" and hierarchical model architectures such as convolutional neural networks. In particular, such systems automatically learn the important features via an automatic error-correction scheme such as back-propagation. Here, the term "big data" refers to a large scale plurality of ophthalmic images representing various instances and stages of ophthalmic pathology, including normal eyes.

There has been instance where ophthalmic images have been used for automated diagnosis of ophthalmic disease. However, such instances have been based on explicit construction of features such as edge-maps which are subsequently piped into classifiers such as support vector machines. This is problematic because, there is consensus that in the image classification problem, hierarchical end-to-end approaches such as convolutional neural networks are generally superior to explicit feature-engineering approaches. Furthermore, within the end-to-end approaches, ensemble strategies have shown some advantage over non-ensemble approaches. In the ensemble approach, a plurality of models are trained and the output class prediction of a sample image is determined as a function of the class prediction of all the models in the ensemble.

There has been instance were ensemble hierarchical end-to-end approaches have been proposed for retinal image classification. However, one major problem with some of these instances is that they propose choosing the 'best' performing architecture of the ensemble. Of note, the 'best' performing architecture of an ensemble depends on the particular dataset on which the trained networks are tested (and trained). Hence overfit is a pitfall of selecting the architecture which performs best on the available test data set. It is well known in the machine-learning community that the best performer on the available test dataset may often not be the best performer in the field, hence a method with more sophisticated regularization would typically provide better generalization in the field.

Other past effort has been based on choosing the non-weighted average of the ensemble. However, a non-weighted averaging ensemble approach is based on blind averaging—i.e., assigning each model in the ensemble an equal weight in effect—and can itself undermine generalization performance in the field. This can occur because in effect, by equally weighting all models, a non-weighted averaging ensemble may be giving relatively too much influence to models which perform poorly in the testing environment and relatively too little influence to models which perform well in the testing environment. A non-weighted averaging ensemble approach is therefore also potentially problematic.

Prior to this disclosure, there were no weighted-ensemble end-to-end methods for ophthalmic disease classification from images.

OBJECTS OF THE INVENTION

It is an object of this invention to provide a system of automated detection of ophthalmic disease, which leverages the computational and algorithmic advantages of hierarchical end-to-end supervised learning approaches.

Furthermore, it is an object of this invention to circumvent the portion of the overfitting problem that results from choosing the machine learning algorithm of an ensemble which performs best on the available finite test data set.

Furthermore, it is an object of this invention to not assign relatively too much weight to models which perform poorly in the testing environment; and to not assign relatively too little weight to models which perform well in the testing environment.

Yet other objects, advantages, and applications of the invention will be apparent from the specification and drawings included herein.

SUMMARY OF THE INVENTION

The invention disclosed herein consists of a means to collect and store images of the eye or some of its parts; by way of example and not limitation, this can include fundus cameras, fluorescein angiography devices, corneal topography devices, visual field machines, optic disc cameras, smart-phone cameras, specialized camera devices for visualizing particular parts of the eye (e.g. anterior chamber angle camera), optical coherence tomography (OCT) machines, BSCAN ultrasonography machines, or computed tomography (CT) machines, and in each case the associated hardware and software for storing and processing images. The images can be stored in any number of image data formats such as JPEG, TIFF, PNG, etc. Furthermore, the images can be stored in three channel (RGB or other tricolor format) or in grayscale formats.

A large scale plurality of the output of such a system is collected and labeled by one skilled in the art of ophthalmic diagnosis, for example an ophthalmologist, optometrist, or any other practitioner or individual with the requisite knowledge and skill to accurately label the images. The labels are stored themselves as a dataset which is mapped one-to-one to the set of images, in the sense that each image has an associated label and vice versa. Each label encodes some or all known ophthalmic diseases which are recognizable from the associated image.

Examples of the ophthalmic diseases that could be apparent on the images and thereby encoded in the labels by the expert include but are not limited to: orbital fractures, exophthalmos, orbital adnexal tumors, ptosis, astigmatism, myopia, hyperopia, corneal ectasias, keratoconus, pellucid marginal degeneration, keratoglobus, microcornea, sclerocornea, congenital glaucoma, corneal hydrops, angle closure glaucoma, anatomically narrow angles, narrow angle glaucoma, mesodermal dysgenesis syndromes, microspherophakia, aniridia, zonular dehisciences of the lens, lenticular dislocation, lenticular subluxation, cataracts, tumors of the cilliary body, diabetic macular edema, non-proliferative diabetic retinopathy, proliferative diabetic retinopathy, non-exudative age-related macular degeneration, exudative age-related macular degeneration, adult vitelliform macular dystrophy, pigment epithelial detachments, cystoid macular edema, vitreous hemorrhage, retinal detachment, retinoschisis, retinal tears, vitreomacular traction, vitreomacular adhesion, lamellar macular holes, full thickness macular holes, epiretinal membranes, pathological myopia, myopic tractional schisis, choroidal nevi, choroidal melanomas, retinoblastoma, other retinal or choroidal tumors, vitritis, and posterior vitreous detachments, optic disc pits, optic disc edema, disc drusen, optic nerve meningioma, optic nerve gliomas, cavernous hemangioma of the orbit, orbital dermoids amongst others.

Certain modalities are particularly suited to certain diseases. For instance, BSCAN ultrasounds (in combination with fundus photographs) are particularly useful at imaging choroidal melanomas in the periphery, while OCT imaging is particularly suited for detecting conditions such as exudative macular degeneration and diabetic macular edema. Nonetheless, there is significant overlap between the utilities of the various modalities. For example, choroidal nevi or melanomas in the macula would be well suited in some respects for OCT imaging—in particular for the detection of subretinal fluid, pigment distortion, or overlying drusen. Furthermore, as the imaging modalities evolve and improve, more uses and applications of the invention disclosed herein will become apparent. Already, high frequency BSCAN ultrasonography is showing great utility and resolution in areas not traditionally thought of as the domain of the BSCAN, such as in more anteriorly located structures. Similarly, with enhanced flexibility and control of laser wavelengths, the regime of OCT imaging is increasing, with lower frequency laser scans yielding increased depth, for instance, and allowing the visualization of choroidal structures. Computed tomograms (CT) scans are particularly useful in visualizing the orbit and its contents. The disclosed invention is able to absorb and immediately utilize any existing ophthalmic imaging modalities, as well as any future adaptations, derivatives, or progeny of imaging modalities.

The ophthalmic images are formatted, standardized, and collated. This step can be done on any number of programming or image processing platforms. The processing steps could include resizing of the image, normalization of the pixel intensities, arranging the shape in the desired order of block parameters such as number of images (N), height of images (H), width of images (W), and color (C) of the images. For example, NHWC. The color of the images can also be standardized to all grayscale or all tricolor. Of note, depending on the application, varying degrees of heterogeneity in the data format may be desired and accommodated as well.

The processed and collated ophthalmic image data is then partitioned into sets for training and for testing. The training and test sets can be further batched for purposes of memory use optimization. The ordering of the images in the sets are randomized to decrease any clustering biases which the learning algorithm may learn. Such clustering bias would be an artifactual feature that would decrease generalization of the trained model. The one-to-one mapping of images to image labels is preserved throughout all the previous steps of preprocessing and randomization.

In the invention disclosed herein, an ensemble of hierarchical end-to-end model architectures are designed. Each of the models in the ensemble are then trained on the training data, and each of them are subsequently tested on the test data. The performance of each model on the test dataset is noted, ranked, and stored. A weight is assigned to each model according to its rank, such that the higher a model's performance on the test data, the higher the weight assigned to that model. In some embodiment of the invention, the weights can be normalized so that they sum up to unity. The ensemble at this point is considered trained. When now presented with an ophthalmic image ("subject image") not previously encountered, the classification task proceeds as follows: For the subject image, the class prediction of each model in the ensemble is computed in the form of a probabilistic class score. Next, for each model, the model's assigned weight is multiplied by the class score of the subject image. The sum of all such products is taken and that sum is divided by the number of models in the ensemble. In other words, the weighted average of class scores is computed and is taken as the ensemble class score of the subject image.

In the invention disclosed herein, various types of hierarchical end-to-end models can be designed as members of the aforementioned ensemble. An example of such a model architecture is a convolutional neural network consisting of multiple layers. A subset of the initial block of layers is characterized by a convolution operation which is done with a weight filter across the input image. These layers are called the convolutional layers. Another type of layer which we will call an interleaving layer can consist of any one of a number of processing modules which guide the feature selection process. These interleaving layers primarily serve as regularization layers. The various types of processing modules are named for the process they conduct and include but are not limited to: batch normalization layers, pooling layers, and drop-out layers. The terminal segment of the architecture is called the dense fully connected layer. This segment is essentially a multilayer perceptron. Its layers consist of multiple nodes and each node in a given layer receives input from all nodes in the preceding layer. The dense fully connected layer terminates in "n" output nodes where "n" is the number of classes in the classification problem. Of note the model architecture can contain any number of the aforementioned layers in any arbitrary configuration. Furthermore, the convolution operation can be replaced by any dot-product type operation through which weights are computed and learned. Other examples of architectural models that can be used include but are not limited to: recurrent neural networks and convolutional recurrent neural networks. In contrast to feed forward networks, in recurrent neural networks the hierarchy can be thought of as applying only locally.

Activation functions are a component of the model architectures. The out-put of each layer is passed as argument into an activation function whose output is in turn passed to the appropriate recipient(s) in the next layer. The activation function will most often be non-linear but can also be chosen to be linear if need be. Examples of activation functions include but are not limited to: Rectified Linear Unit (ReLU), leaky Rectified Linear Unit or "leaky ReLU", softmax function, sigmoid function, or tanh function amongst others. The softmax function lends itself to probabilistic interpretation and is therefore of particular utility at the output nodes of the fully connected layers.

An exemplary outline of the training and testing steps of the individual models in the ensemble is as follows: ophthalmic images are collected, labeled, and partitioned into a training set and a test set. During the training phase weights are initialized for the convolutional filters and the neural network interconnections in the architecture. For each image, a forward pass is made through the model architecture by convolving the filter over the image and applying the activation function to generate a feature map. This is done for each of the filters in the system, generating a number of feature maps equal to the number of filters. Interleaving steps such as pooling, batch normalization, or drop-out are conducted wherever prescribed in the architecture. Convolution is also done however number of times and wherever specified in the architecture. The net output of these feature extraction steps is called a feature vector which is passed as input into the classification phase encoded by fully-connected layer. This culminates in the predicted classification which is compared to the target label. The resulting error—determined by a chosen loss function—is propagated backwards using some form of back-propagation method (i.e., reverse chain-rule) to compute the influence of each weight on the loss. In particular, the rate of change of loss with respect to each weight is determined. This in turn is used to update the weights in a direction to decrease the loss. This process of forward pass then back-propagation is repeated iteratively till the loss decreases below a prescribed level, or till a prescribed stopping point is reached. Of note, the above steps and methods can be changed or modified to generalizations that convey the intent of the task. Once the training is completed, the determined weights are stored, as is the constructed model architecture. A previously unseen ophthalmic image can then be classified by passing it as input into the network and running a forward pass.

In summary, the invention disclosed herein consists of systems and methods to design and use an ensemble of hierarchical end-to-end models to classify ophthalmic images according to disease state and stage. The models in the ensemble are each trained on a training dataset and tested on a test dataset. The models are then ranked according to their performance on the test dataset, and weights are assigned proportional to rank. Newly presented images are classified by each model individually, generating one class score per model. The rank-based weights are then used to compute a weighted average of the class scores, according to which the image is classified.

The invention consists of the several outlined processes below, and their relation to each other, as well as all modifications which leave the spirit of the invention invariant. The scope of the invention is outlined in the claims section.

BRIEF DESCRIPTION OF THE DRAWINGS

In the following detailed description of the invention, we reference the herein listed drawings and their associated descriptions, in which.

DETAILED DESCRIPTION OF THE PREFERRED EMBODIMENTS

Figure 1:
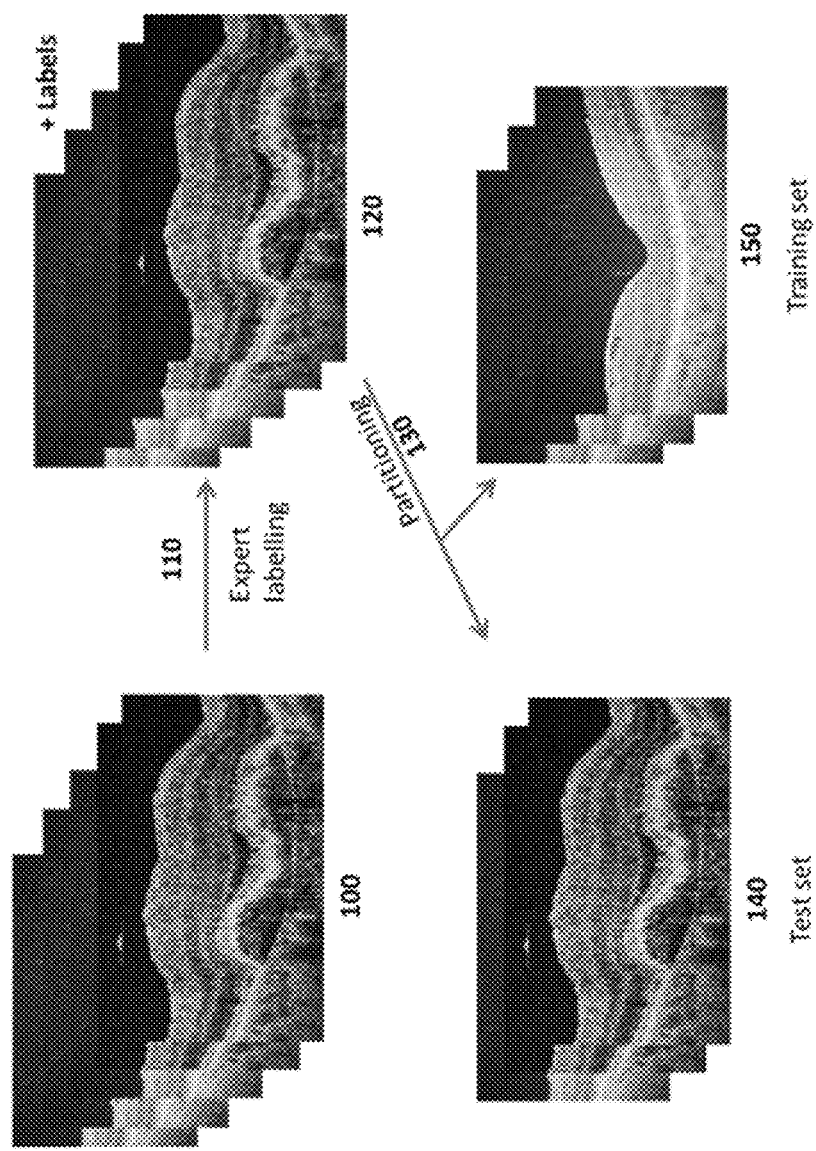
FIG. 1 is a schematic of tomogram pre-training processing.

The illustration in FIG. 1 is a preferred embodiment of the pre-training processing steps carried out on the data. The schematic includes an unlabeled set of images 100. In step 110, the unlabeled data in 100 is labeled by an expert or some other entity with sufficient knowledge to do so competently. This labeling yields a labeled data set depicted in 120. In the step 130 the labeled data set 120 is partitioned into a training set, 150, and test data set, 140. The choice of partitioning fraction is itself a learnable hyper-parameter—in the sense that various fractions can be tried empirically to determine the fraction with best most generalizable results. Various forms of pre-processing such as data augmentation and random shuffling can be done to the data set of labeled images 120 to yield a data set of processed tomograms. The processed and labeled images are then partitioned into a training set, 150, and a test set, 140. In turn, the training and test sets are entered as input into each of the machine learning models that comprise the ensemble.

Figure 2:
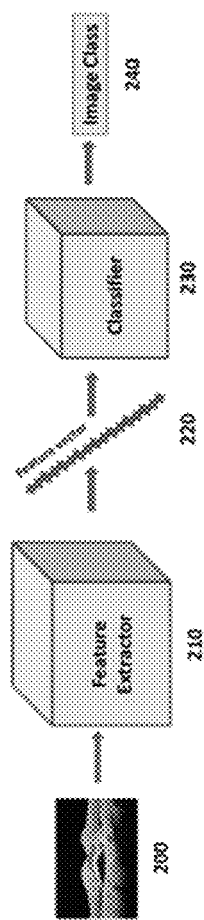
FIG. 2 Feature extraction and classification scheme.

The depiction in FIG. 2 is an exemplary schema of a model of the ensemble. In this one embodiment, the ophthalmic image, 200, is accessed by a feature extraction mechanism, for example by convolutional operations characteristic of convolutional neural networks. In FIG. 2, the feature extraction mechanism is represented by 210. The output of the feature extraction mechanism is a feature vector or other mathematical object which encodes the features of the ophthalmic image. In what preceded and in what follows, the term feature vector is understood to mean either a mathematical vector or any other mathematical object that encodes the features of the ophthalmic image. In FIG. 2 the feature vector is represented by 220. The feature vector is then acted on by a classification mechanism, for example, the fully connected layers characteristic of convolutional neural networks or other multilayer perceptron based schemes. In FIG. 2 the classification mechanism is represented by 230. The output of the classification process is a choice of image class, as depicted in 240. Of note, this choice of image class can take on various forms including probabilistic as in cases where the softmax activation function is used in the output.

Figure 3:
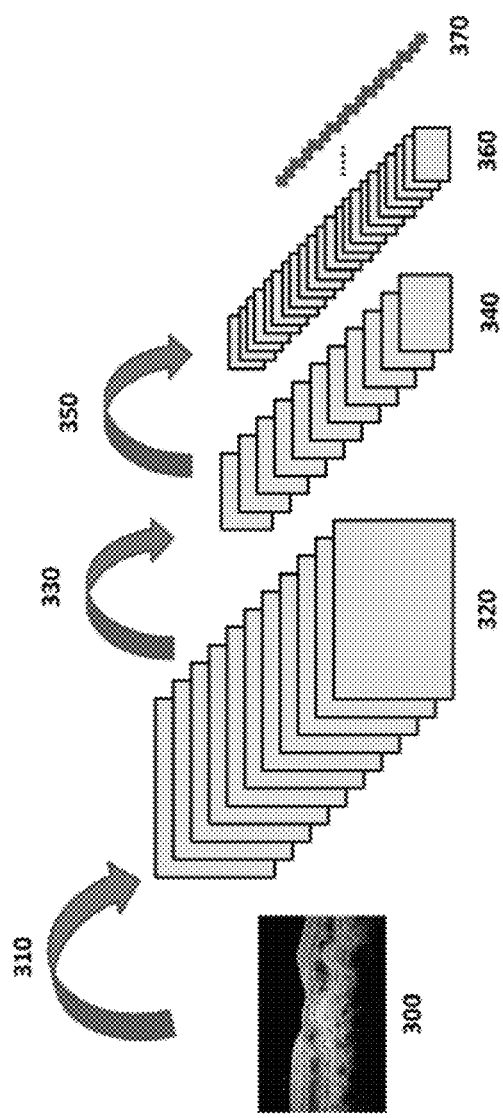
FIG. 3 Convolutional Layers.

In some embodiment of the invention, some of the members of the ensemble can be convolutional neural networks (CNNs). An exemplary illustration of a feature extraction scheme of a CNN is depicted in FIG. 3. The scheme takes an ophthalmic image as input, as depicted in 300. A set of feature extraction operations are then carried out on the ophthalmic image. This typically would involve some generalization of the dot product, but can use other process instead. In the case of convolutional neural networks, for example, this dot product step uses the convolution operation. In FIG. 3, the first of these set of feature extraction operations is depicted by 310 and yields 320. Of note, 320 is a set of feature maps whose number is equal to the number of convolutional filters. Each of the feature maps shown in 320 is generated by doing convolution operations on 300 using a distinct filter. The convolution operation is further exemplified in FIG. 4 below. Each of the feature maps in 320 in turn serves as an input image for a similar type of dot-product operation 330 and in turn yields a next layer of feature maps as depicted in 340. The dot product operation yielding the subsequent feature map can be done any arbitrary—up to a point—number of times as depicted e.g., as in 350 yielding 360, and so on. The actual number of times the dot product can be done may be limited by the relative size of the input image in comparison to the filter. The number of times the operation is applied and the forms of the operation can be chosen to optimize the classification performance of the architecture. The end product of the feature extraction steps is a feature vector or other object encoding the image features. Here, that object is represented by 370.

Figure 4:
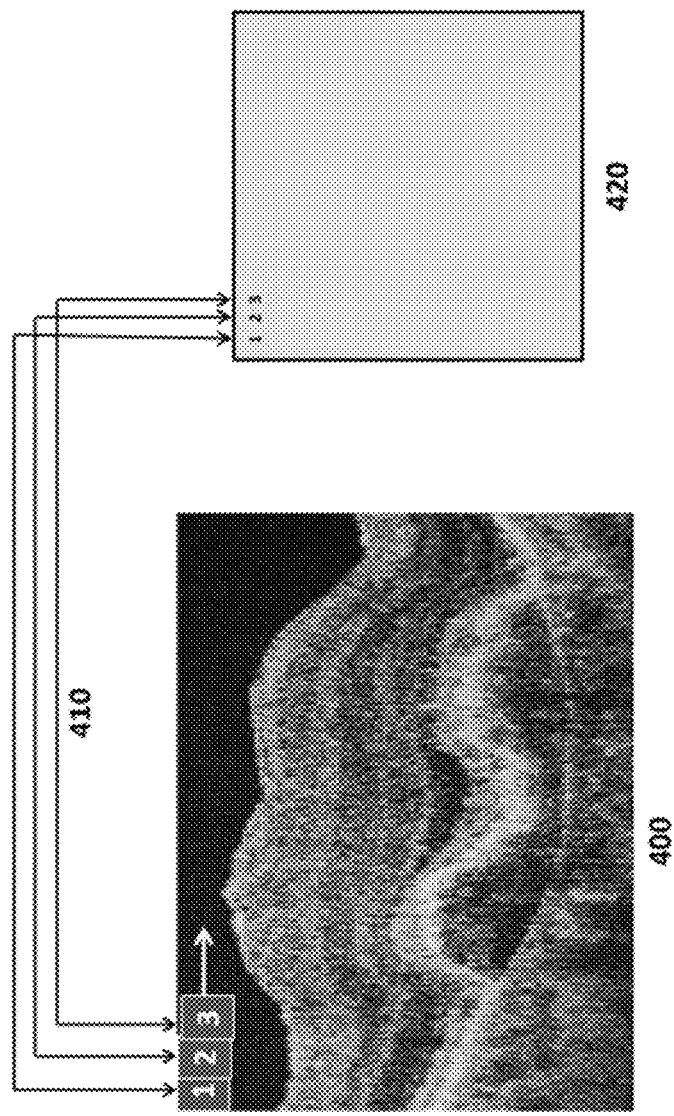
FIG. 4 Convolution Operation.

Depicted in FIG. 4 is a convolution operation. In this example, the operand is the ophthalmic image depicted in 400. At the top left corner of this ophthalmic image is an illustration of the positions of a given convolutional filter. Each position is offset from the next by a prescribed stride. A prescribed dot product operation is then conducted, such as pixel-wise multiplication followed by summation of all the products, as in the following equation:

$$c_k = \Sigma u_i v_{i,k} \quad (1)$$

where $u_i$ is the ith pixel value in the filter, $v_{i,k}$ is the ith pixel value of the portion of the ophthalmic image that overlaps the filter when the filter is in the kth position. And $c_k$ is the value of the kth pixel of the generated feature map. The multiple overlapping positions of the filter can be thought of as the filter scanning over the ophthalmic image and performing the aforementioned computations as it does so. In FIG. 4 this scanning is represented by 410, and the generated feature map is represented by 420.

Figure 5:
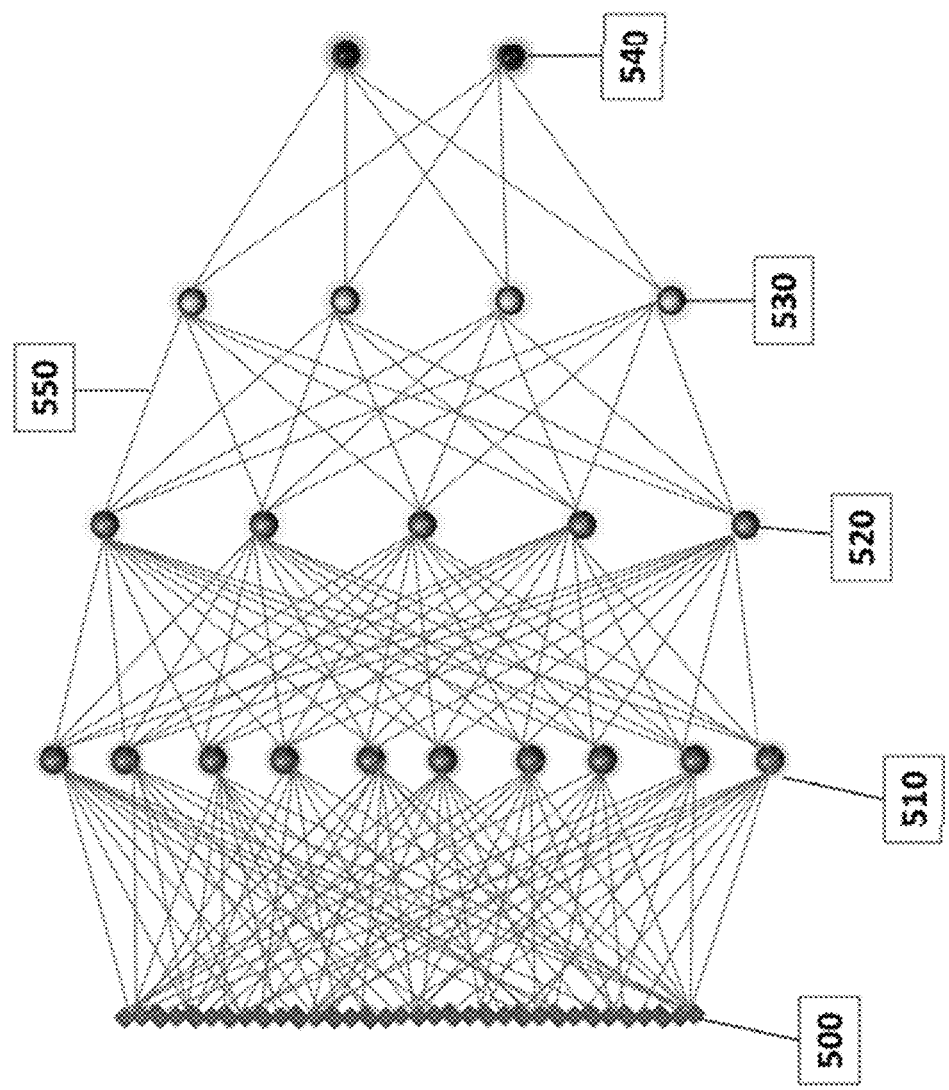
FIG. 5 Fully Connected Layer.

In some embodiment of the invention, the ensemble contains some machine learning models whose classification mechanisms are multilayer perceptrons—also known as fully connected layers. An exemplification of such a fully connected layer is depicted in FIG. 5. The input is a feature vector represented by 500. This is connected to the first hidden layer 510. Each neuron of this layer is connected to every neuron of the next hidden layer, 520. This pattern continues sequentially into the output layers 540. The weighted interconnections between nodes are depicted by lines as exemplified in 550.

Figure 6:
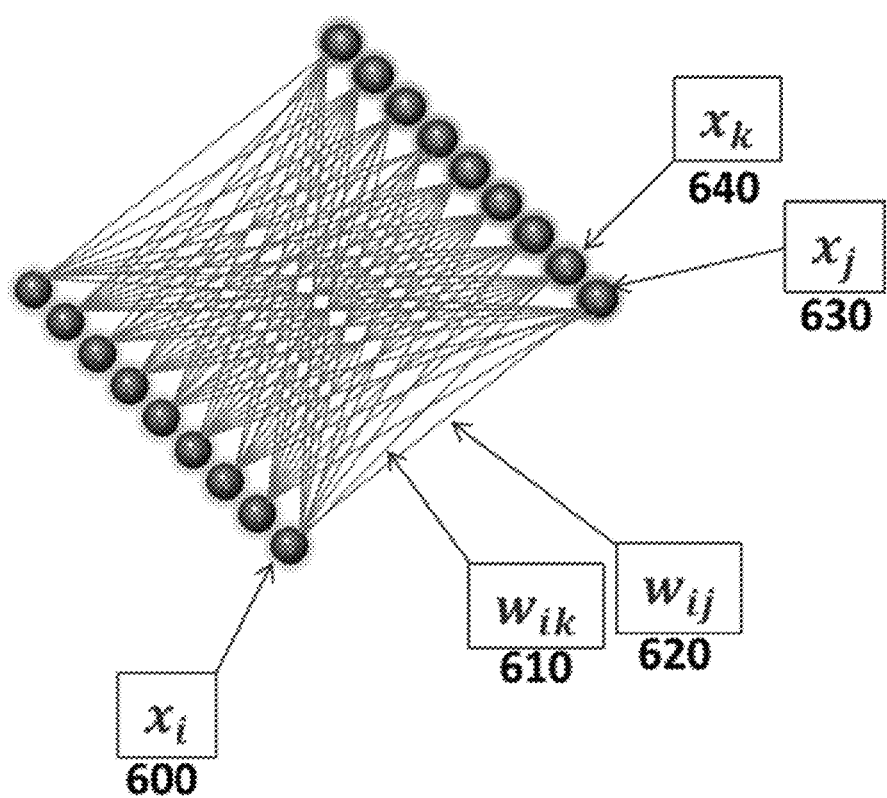
FIG. 6 View of inter-layer connection.

The depiction in FIG. 6 illustrates an exemplary configuration of a preferred embodiment of a single sublayer of the fully connected layer. The representation in FIG. 6 contains examples of network nodes or "neurons" depicted by 600, 630, and 640. The representation in FIG. 6 also contains examples of weights or multiplicative coefficients associated with each connection between any two network nodes. In particular, one sees weight 620 between nodes 600 and 630, and weight 610 between nodes 600 and 640.

Figure 7:
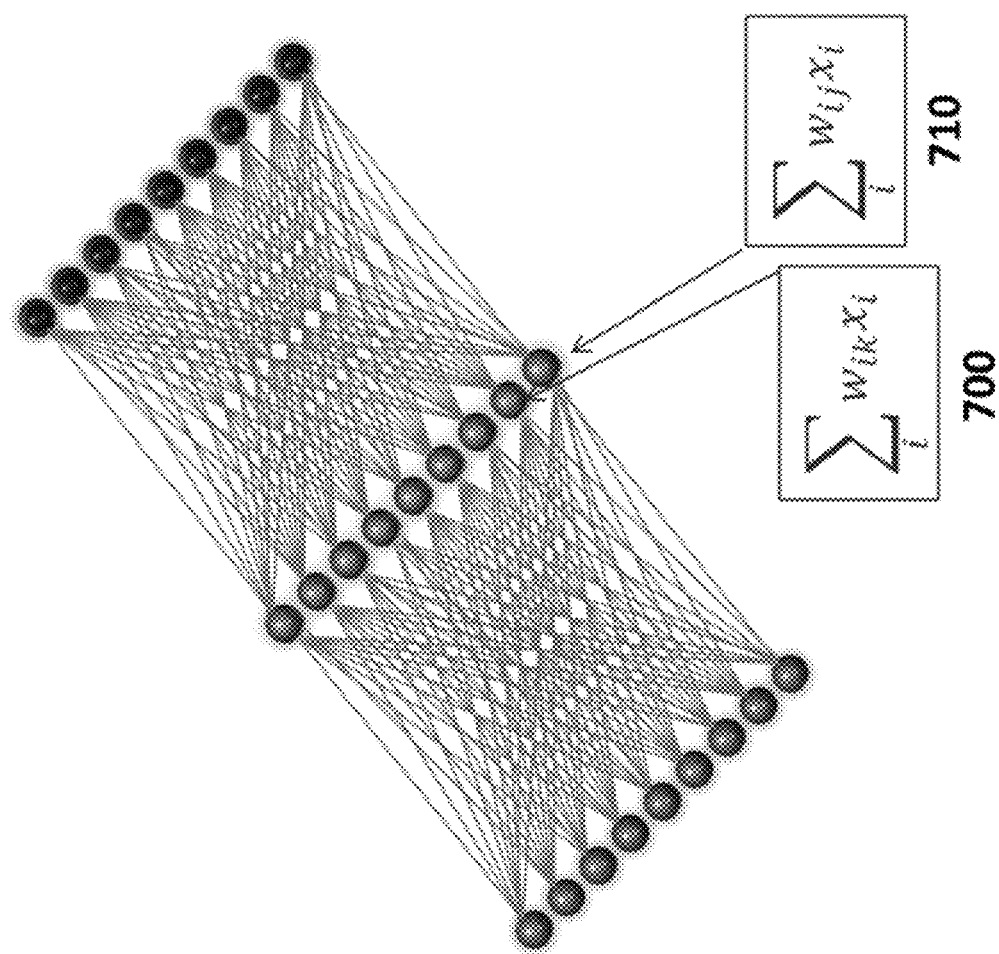
FIG. 7 is an example of two connected sublayers of a fully connected layer.

The depiction in FIG. 7 illustrates an exemplary computation during a forward pass. In particular, the labeled equations demonstrate the linear combination of weighted inputs between sublayers in the fully connected layer. The general mathematical expression for this step is given by:

$$\sum_{i=1}^{n} w_{ij} x_i, \quad (2)$$

where $\chi_\alpha$ denotes the output from neuron $\chi_\alpha$, $w_{ij}$ is the weight connecting neuron $\chi_i$ to neuron $\chi_j$, and n is the number of neurons providing input into neuron $\chi_j$, such as is depicted in 710 of FIG. 7. Similarly, the expression for the input into neuron $\chi_k$ is shown in 700.

Equation (2) and its type are then subsequently fed as input into an activation function $\sigma(\chi)$ such as ReLU for example but not limitation, yielding the following form:

$$\sigma\left(\sum_{i=1}^{n} w_{ij} x_i\right) \quad (3)$$

Figure 8:
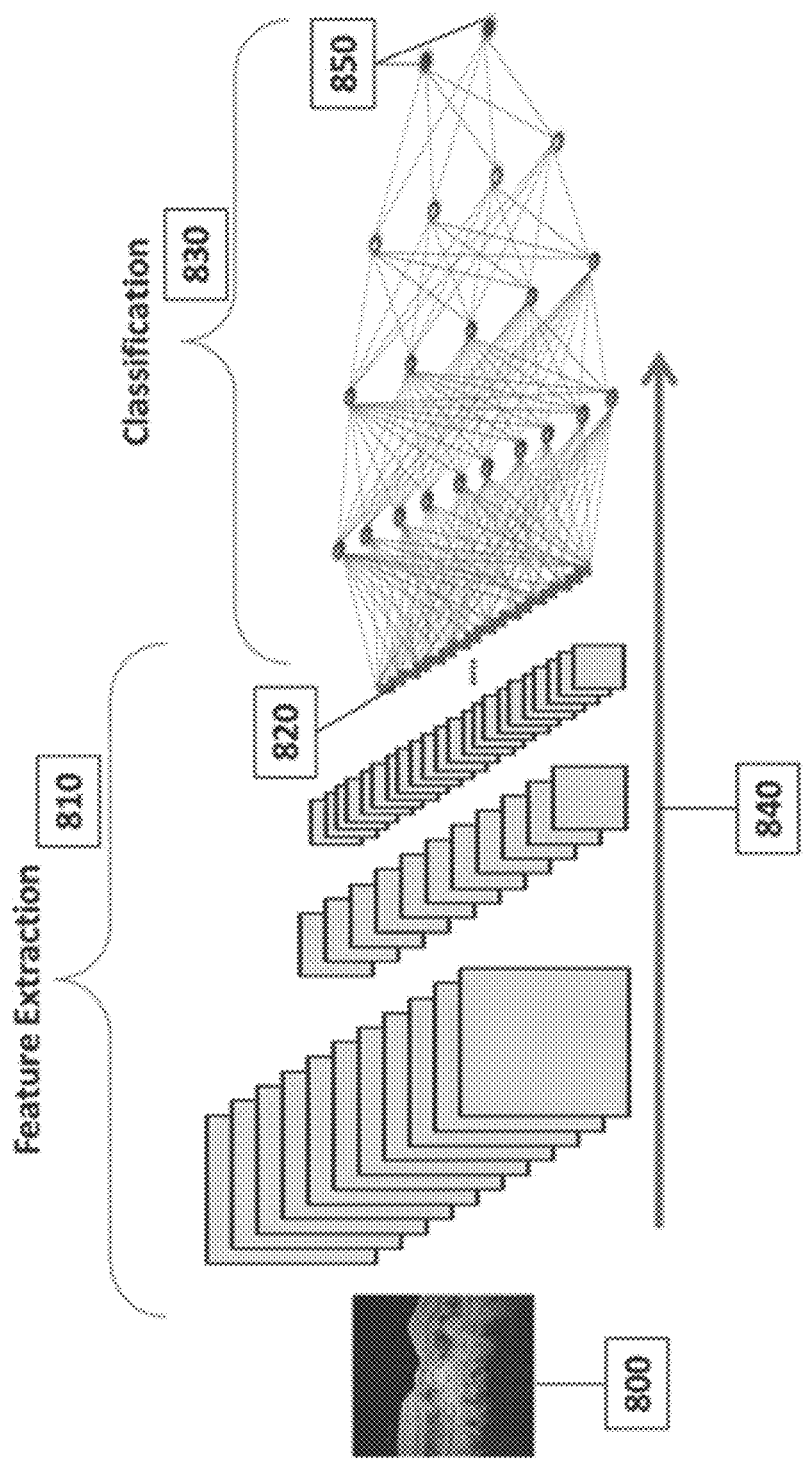
FIG. 8 is an example of a convolutional neural network.

An exemplary method by which an individual model of the ensemble performs feature extraction and subsequent classification is depicted in FIG. 8. This particular example is a convolutional neural network. Other architectures like recurrent neural networks, convolutional recurrent neural networks, and various hybrids and ensembles of diverse architectures can be used. In this particular example shown in FIG. 8, the feature extraction part is depicted in 810 while the classification part is depicted in 830. The direction of operations is depicted by 840. The initial forward pass consists of the following steps:

1. The filter weights and the fully connected layer weights are initialized either randomly or using some prior knowledge such as a pre-trained model.
2. Using the initialized filter weights, a dot product of the ophthalmic image, 800, and the filter is taken.
3. This yields the feature maps shown, upon whom sequential applications of a dot product yields the feature object depicted in 820.
4. The feature object is acted upon by the classification scheme to yield an estimate of the image class, as depicted by 850.
5. The image class estimated by the algorithm is compared to target values stored in the label. The net extent of the estimation error across classes is quantified by a loss function, for example hinged loss or other variant. We then proceed to iteratively minimize the loss or net error, as described in FIG. 9 below.

The error computed above is the objective function which we seek to minimize. An example is as follows:

$$\text{Loss}\left(\left\{\hat{y}_p - \rho\left(\sum_t w_{tp}\left(\cdots \sum_k w_{kl}\left(\gamma\left(\sum_k w_{jk}\left(\sigma\left(\sum_i w_{ij} x_i\right)\right)\right)\right) \cdots \right)\right)\right\}_p\right), \quad (4)$$

where $\chi_i$ are the input features; w are weights; $\sigma$, $\gamma$, $\rho$ are activation functions; and $\hat{y}_p$ is the target value of the pth class. Of note L is a composite function consisting of the weighted linear combinations of inputs into each successive layer. The effect of any given weight on the net loss can therefore be computed using the chain rule. For instance, we can re-write the loss function in the notationally concise functional form $$L(w)=b(c(d(\ldots i(j(w))))), \quad (5)$$

where w is a weight and b, c, d, . . . , i, j are functions describing the network. Then the effect of weight w on loss L, denoted $$\frac{\partial L}{\partial w},$$

is given by $$\frac{\partial l}{\partial w} = \frac{\partial L}{\partial b}\frac{\partial b}{\partial c}\frac{\partial c}{\partial d} \cdots \frac{\partial i}{\partial j}\frac{\partial j}{\partial w} \quad (6)$$

Figure 9:
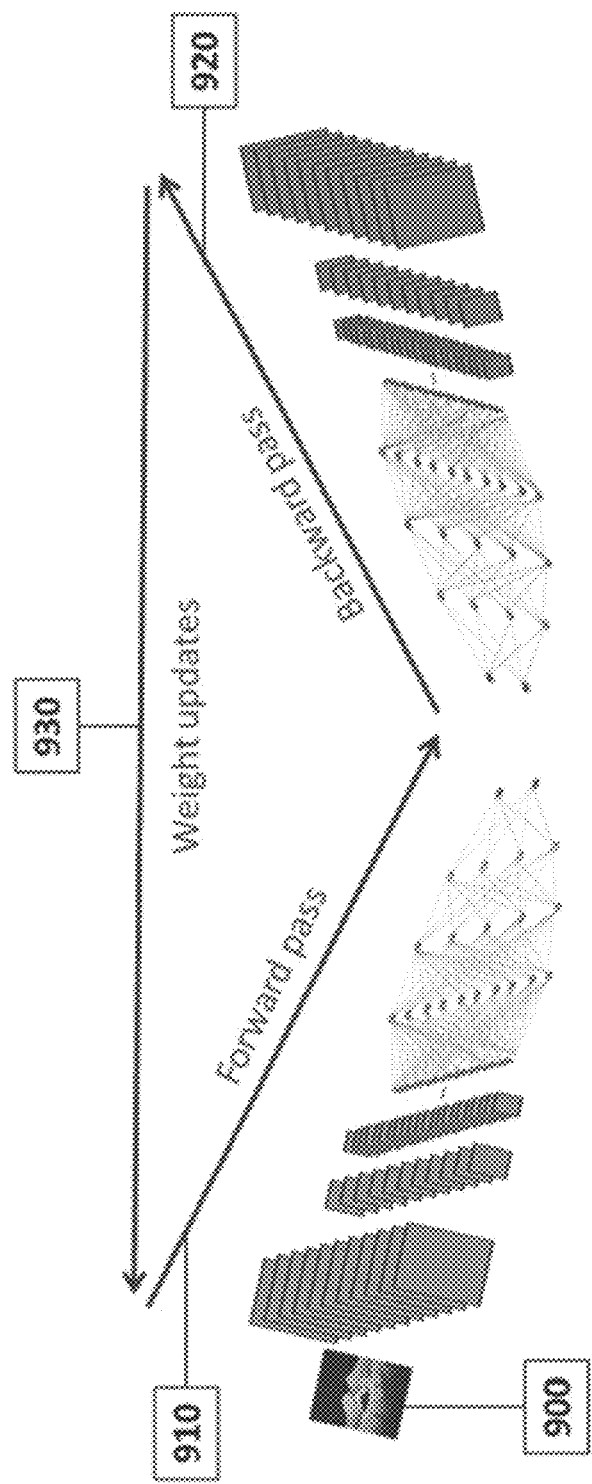
FIG. 9 is an example of the iterative training scheme.

This is done in a computationally efficient manner using the well-known back-propagation algorithm. In some preferred embodiment of the invention disclosed herein, an ophthalmic image input is obtained and the training procedure is carried out in an iterative manner as shown in FIG. 9. An ophthalmic image is shown in 900 —in this case illustrated, it is an OCT image of the macula. The forward pass is done as shown in 910. A loss is determined and used as input into the back-propagation phase depicted in 920. The back-propagation determines the influence of each weight on the loss. This information is then used in phase 930 to update the weights in the indicated direction, i.e., to decrease the loss. Once the weights are updated, the forward pass is repeated to determine the new loss, which in turn is passed again as input into the back-propagation phase and so on. The procedure proceeds iteratively as noted till a prescribed stopping point, i.e., till the loss is below a prescribed amount or till the cycle has repeated a preset number of times.

Figure 10:
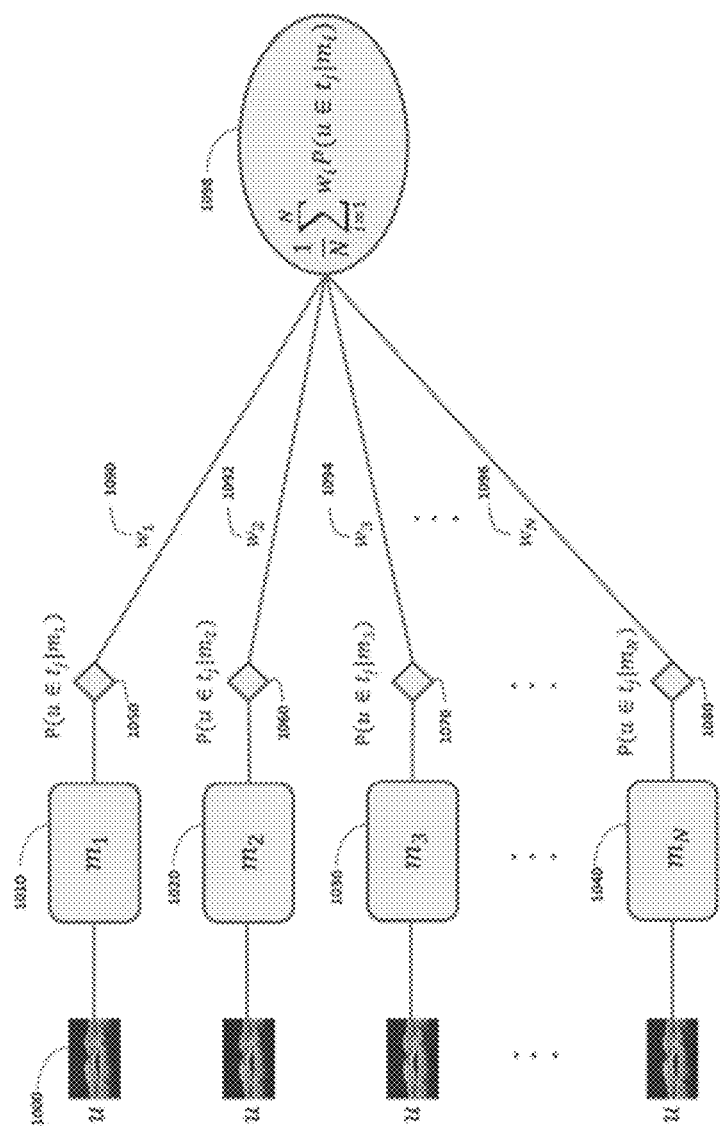
FIG. 10 Weighted Averaging of Ensemble.

FIG. 10 illustrates by way of example, a weighted averaging procedure of the invention disclosed herein. 1000 depicts a subject ophthalmic image to be classified by the disclosed method. There are N number of models—1010, 1020, 1030, 1040—in the ensemble, where N can be any number. Training of the models are as exemplified above. Of note, the models in the ensemble can be chosen or designed based on any number of criteria including but not limited to level of performance on a test dataset, heuristic criteria such as depth and complexity of model architecture, known good performance on other types of datasets and problem domains—where "good" can be defined as desired. 1050 is the probability predicted by model 1, 1010, that ophthalmic image u 1000 is of class $t_j$. We represent this with the notation, $$P(u \in t_j|m_1). \quad (7)$$

Similarly, 1060 is the probability predicted by model 2, 1020, that ophthalmic image u 1000 is of class $t_j$, 1070 is the probability predicted by model 3, 1030, that ophthalmic image u 1000 is of class $t_j$, and 1080 is the probability predicted by model N, 1040, that ophthalmic image u 1000 is of class $t_j$. Model weights are determined based on performance of the individual models on test data. Any number of order preserving weight assignment schemes can be applied, such that the better the relative performance of a model, the higher its assigned weight. The weight assignment scheme can include a performance threshold below which a weight of zero is assigned, i.e., models with low enough performance can be excluded from the voting. In FIG. 10 the weights 1090, 1092, 1094, and 1096 are associated with models 1010, 1020, 1030, and 1040 respectively. The weighted average as shown in 1098 is $$\frac{1}{n}\sum_{i=1}^{n} w_i P(u \in t_j|m_i) \quad (8)$$

Figure 11:
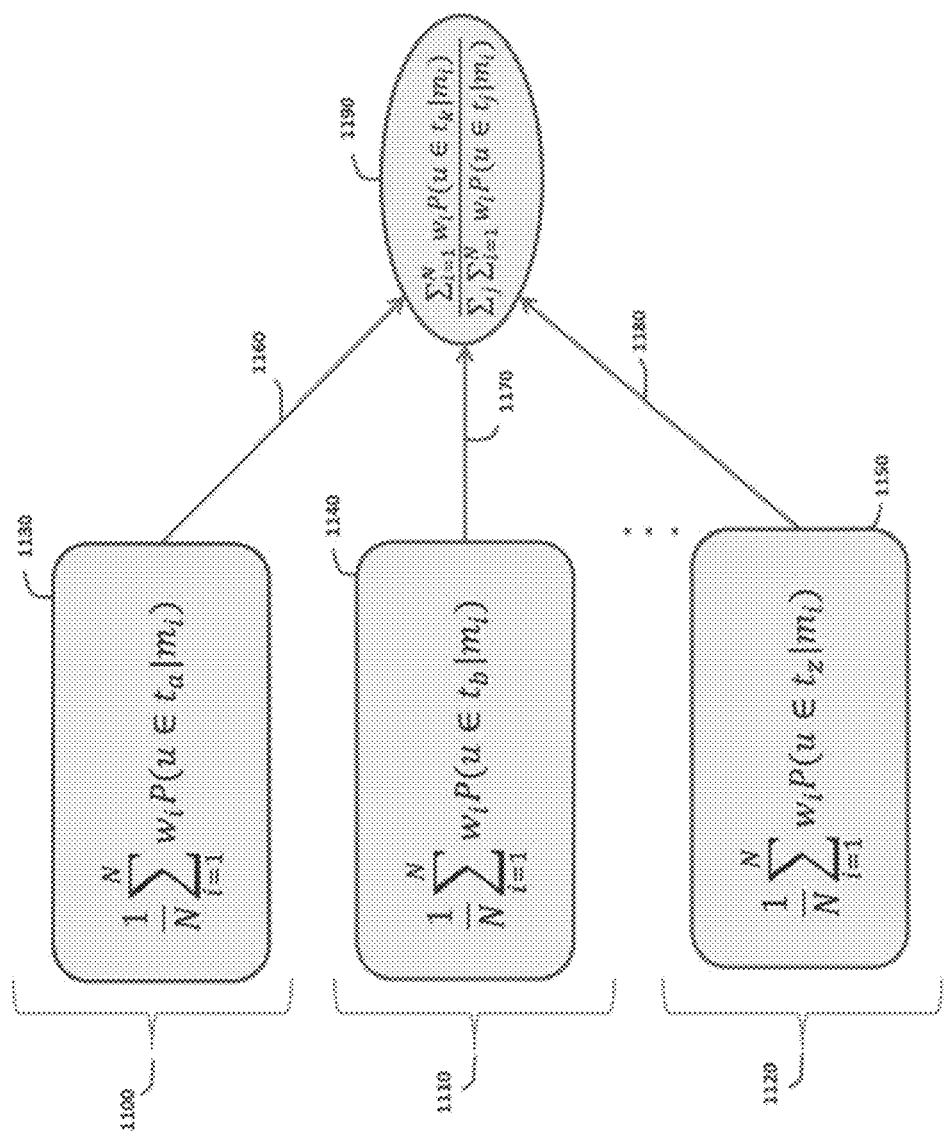
FIG. 11 Weighted Ensemble Class Score Computation.

In FIG. 11, 1100 represents the process for computing the weighted average of the probabilities that the subject image belongs to class 1. Similarly, 1110 represents the process for computing the weighted average of the probabilities that the subject image belongs to class 2, and 1120 represents the process for computing the weighted average of the probabilities that the subject image belongs to class N. The respective weighted averages are depicted in 1130, 1140, and 1150. The weighted averages are passed along in steps 1160, 1170, and 1180 for normalization and computation of the class scores predicted by the weighted-ensemble. By way of example, 1190 depicts the probability that image u belongs to class $t_k$, i.e., $$P(u \in t_k|m_1, m_2, m_3, \ldots, m_N) = \frac{\sum_{i=1}^{N} w_i P(u \in t_k|m_i)}{\sum_{j}\sum_{i=1}^{N} w_i P(u \in t_j|m_i)} \quad (9)$$

The denominator in the above equation is the normalization factor that makes weighted-ensemble class scores a distribution, i.e., sum to unity. In contrast to the loss function—whose evaluation can be negative, and hence can require for exponentiation (or similar mechanism) to ensure positivity and to allow for the formation of a distribution. Here, each of the individual model predictions are typically already probabilities, i.e., non-negative and in [0, 1].

Figure 12:
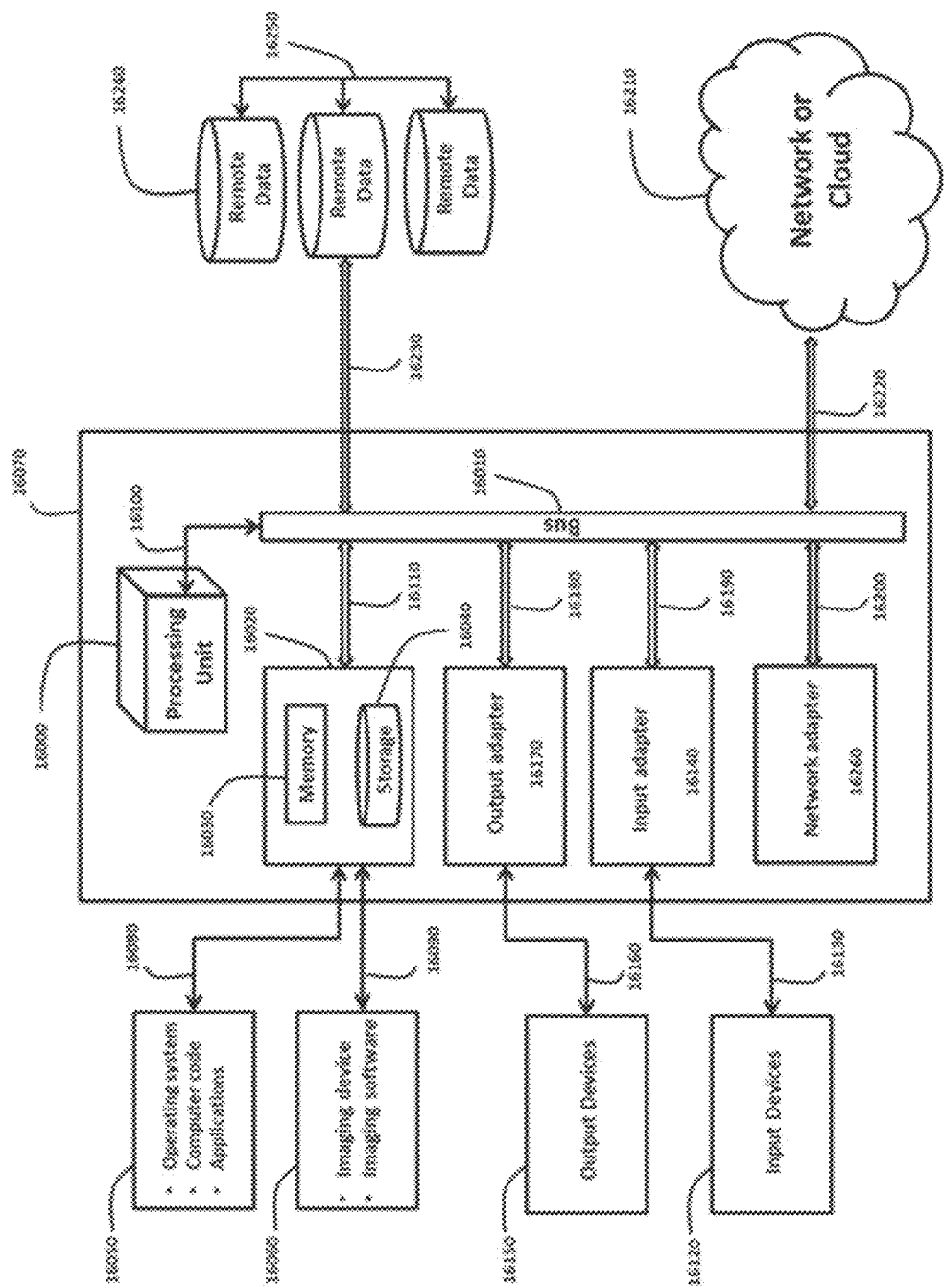
FIG. 12 Computing environment.

Ones skilled in the art will recognize that the invention disclosed herein can be implemented over an arbitrary range of computing configurations. We will refer to any instantiation of these computing configurations as the computing environment. An exemplary illustration of a computing environment is depicted in FIG. 12. Examples of computing environments include but are not limited to desktop computers, laptop computers, tablet personal computers, mainframes, mobile smart phones, smart television, programmable hand-held devices and consumer products, distributed computing infrastructures over a network, cloud computing environments, or any assembly of computing components such as memory and processing—for example.

As illustrated in FIG. 12 the invention disclosed herein can be implemented over a system that contains a device or unit for processing the instructions of the invention. This processing unit 16000 can be a single core central processing unit (CPU), multiple core CPU, graphics processing unit (GPU), multiplexed or multiply-connected GPU system, or any other homogeneous or heterogeneous distributed network of processors.

In some embodiment of the invention disclosed herein, the computing environment can contain a memory mechanism to store computer-readable media. By way of example and not limitation, this can include removable or non-removable media, volatile or non-volatile media. By way of example and not limitation, removable media can be in the form of flash memory card, USB drives, compact discs (CD), blu-ray discs, digital versatile disc (DVD) or other removable optical storage forms, floppy discs, magnetic tapes, magnetic cassettes, and external hard disc drives. By way of example but not limitation, non-removable media can be in the form of magnetic drives, random access memory (RAM), read-only memory (ROM) and any other memory media fixed to the computer.

As depicted in FIG. 12, the computing environment can include a system memory 16030 which can be volatile memory such as random access memory (RAM) and may also include non-volatile memory such as read-only memory (ROM). Additionally, there typically is some mass storage device 16040 associated with the computing environment, which can take the form of hard disc drive (HDD), solid state drive, or CD, CD-ROM, blu-ray disc or other optical media storage device. In some other embodiment of the invention the system can be connected to remote data 16240.

The computer readable content stored on the various memory devices can include an operating system, computer codes, and other applications 16050. By way of example not limitation, the operating system can be any number of proprietary software such as Microsoft windows, Android, Macintosh operating system, iphone operating system (iOS), or Linux commercial distributions. It can also be open-source software such as Linux versions e.g. Ubuntu. In other embodiments of the invention, imaging software and connection instructions to an imaging device 16060 can also be stored on the memory mechanism. The procedural algorithm set forth in the disclosure herein can be stored on—but not limited to—any of the aforementioned memory mechanisms. In particular, computer readable instructions for training and subsequent image classification tasks can be stored on the memory mechanism.

The computing environment typically includes a system bus 16010 through which the various computing components are connected and communicate with each other. The system bus 16010 can consist of a memory bus, an address bus, and a control bus. Furthermore, it can be implemented via a number of architectures including but not limited to Industry Standard Architecture (ISA) bus, Extended ISA (EISA) bus, Universal Serial Bus (USB), microchannel bus, peripheral component interconnect (PCI) bus, PCI-Express bus, Video Electronics Standard Association (VESA) local bus, Small Computer System Interface (SCSI) bus, and Accelerated Graphics Port (AGP) bus. The bus system can take the form of wired or wireless channels, and all components of the computer can be located remote from each other and connected via the bus system. By way of example and not of limitation, the processing unit 16000, memory 16020, input devices 16120, output devices 16150 can all be connected via the bus system. In the representation depicted in FIG. 12, by way of example not limitation, the processing unit 16000 can be connected to the main system bus 16010 via a bus route connection 16100; the memory 16020 can be connected via a bus route 16110; the output adapter 16170 can be connected via a bus route 16180; the input adapter 16140 can be connected via a bus route 16190; the network adapter 16260 can be connected via a bus route 16200; the remote data store 16240 can be connected vis a bus route 16230; and the cloud infrastructure can be connected to the main system bus vis a bus route 16220.

In some embodiment of the invention disclosed herein, FIG. 12 illustrates that instructions and commands can be input by the user using any number of input devices 16120. The input device 16120 can be connected to an input adapter 16140 via an interface 16130 and/or via coupling to a tributary of the bus system 16010. Examples of input devices 16120 include but are by no means limited to keyboards, mouse devices, stylus pens, touchscreen mechanisms and other tactile systems, microphones, joysticks, infrared (IR) remote control systems, optical perception systems, body suits and other motion detectors. In addition to the bus system 16010, examples of interfaces through which the input device 16120 can be connected include but are by no means limited to USB ports, IR interface, IEEE 802.15.1 short wavelength UHF radio wave system (bluetooth), parallel ports, game ports, and IEEE 1394 serial ports such as FireWire, i.LINK, and Lynx.

In some embodiment of the invention disclosed herein, FIG. 12 illustrates that output data, instructions, and other media can be output via any number of output devices 16150. The output device 16150 can be connected to an output adapter 16170 via an interface 16160 and/or via coupling to a tributary of the bus system 16010. Examples of output devices 16150 include but are by no means limited to computer monitors, printers, speakers, vibration systems, and direct write of computer-readable instructions to memory devices and mechanisms. Such memory devices and mechanisms can include by way of example and not limitation, removable or non-removable media, volatile or non-volatile media. By way of example and not limitation, removable media can be in the form of flash memory card, USB drives, compact discs (CD), blu-ray discs, digital versatile disc (DVD) or other removable optical storage forms, floppy discs, magnetic tapes, magnetic cassettes, and external hard disc drives. By way of example but not limitation, non-removable media can be in the form of magnetic drives, random access memory (RAM), read-only memory (ROM) and any other memory media fixed to the computer. In addition to the bus system 16010, examples of interfaces through which the output device 16150 can be connected include but are by no means limited to USB ports, IR interface, IEEE 802.15.1 short wavelength UHF radio wave system (bluetooth), parallel ports, game ports, and IEEE 1394 serial ports such as FireWire, i.LINK, and Lynx.

In some embodiment of the invention disclosed herein some of the computing components can be located remotely and connected to via a wired or wireless network. By way of example and not limitation, FIG. 12 shows a cloud 16210 and a remote data source 16240 connected to the main system bus 16010 via bus routes 16220 and 16230 respectively. The cloud computing infrastructure 16210 can itself contain any number of computing components or a complete computing environment in the form of a virtual machine (VM). The remote data source 16240 can be connected via a network to any number of external sources such as imaging devices, lmagmg systems, or imaging software.

In some embodiment of the invention disclosed herein, an imaging system which captures and pre-processes images, e.g., 16060, is attached directly to the system. Stored in the memory mechanism—16020, 16240, or 16210—is a model trained according to the machine learning procedure set forth herein. Computer readable instructions are also stored in the memory mechanism, so that upon command, images can be captured from a patient in real time, or can be received over a network from a remote or local previously collated database. In response to command such images can be classified by the pre-trained machine learning procedure disclosed herein. The classification output can then be transmitted to the care provider and/or patient for information, interpretation, storage, and appropriate action. This trans-mission can be done over a wired or wireless network as previously detailed, as the recipient of the classification output can be at a remote location.

Illustrating the invention disclosed herein, an anonymized database of 3000 ocular coherence tomograms (OCTs) of the macula was compiled. Binary labels were assigned by an American board-certified ophthalmologist and Retina specialist. The labels were 'actively exudating age-related macula degeneration' or 'not actively exudating age-related macula degeneration'. The database was split into one dataset for training and a separate dataset for validation. 400 OCT images were used for validation—200 'actively exudating' and 200 'not actively exudating'. The algorithm achieved 99.2% accuracy in distinguishing between 'actively exudating' and 'not actively exudating'.

The objects set forth in the preceding are presented in an illustrative manner for reason of efficiency. It is hereby noted that the above disclosed methods and systems can be implemented in manners such that modifications are made to the particular illustration presented above, while yet the spirit and scope of the invention is retained. The interpretation of the above disclosure is to contain such modifications, and is not to be limited to the particular illustrative examples and associated drawings set-forth herein.

Furthermore, by intention, the following claims encompass all of the general and specific attributes of the invention described herein; and encompass all possible expressions of the scope of the invention, which can be interpreted—as pertaining to language—as falling between the aforementioned general and specific ends.

What is claimed:

1. A method for weighted-ensemble training of machine-learning models to classify ophthalmic images according to features such as disease type and state; where the method comprises of:
   a) an ensemble of machine-learning models each of which consists of:
      i. a feature extraction mechanism; and
      ii. a classification mechanism;
   b) a step to split the input data into training and test sets;
   c) a step to initialize the weights;
   d) for each model, a step in which the feature extraction mechanism yields a feature vector or other object encoding the ophthalmic image features;
   e) for each model, a step in which the feature vector is passed into the classification mechanism to yield a class prediction;
   f) for each model, a mechanism to iteratively update the weights to reduce class prediction error;
   g) for each model, a stopping mechanism for the iteration;
   h) a step to compare and rank the models based on their performance on a test dataset;
   i) a step to assign weights to the various models in the ensemble; and
   j) given a subject ophthalmic image, a step to compute the weighted-average of the class predictions of the plurality of models, and to choose the ophthalmic image class based on this weighted-averaging step.

2. The method of claim 1 wherein some model of the ensemble is a convolutional neural network.

3. The method of claim 1 wherein some model of the ensemble is a recurrent neural network.

4. The method of claim 1 wherein a rectified linear unit (ReL U) or leaky ReL U is used as the activation function of hidden layers.

5. The method of claim 1 wherein a softmax function is used as the activation function of the output layer.

6. The method of claim 1 wherein batch normalization is performed.

7. The method of claim 1 wherein drop out regularization is performed in the input layers.

8. The method of claim 1 wherein the weight initialization step utilizes a pretrained model.

9. The method of claim 1 wherein the weight initialization step is based on random assignment.

10. The method of claim 1 wherein the iterative weight update mechanism is backpropagation.

11. The method of claim 1 wherein the stopping mechanism is to proceed iteratively till a preset number of iterations or till a preset prediction performance threshold is reached.

12. The method of claim 1 wherein the method for assigning weights to models is based on model performance rank.

13. The method of claim 1 wherein a pooling step is performed between feature extraction or classification layers.

14. A combined imaging and computing stem, consisting:
    a) a system to capture or retrieve an ophthalmic image;
    b) a computer or computing environment consisting of processing and storage components;
    c) a trained weighted-ensemble of machine learning models stored on the storage component; and
    d) executable commands stored on the storage component such that, upon command,
       i. an ophthalmic image is obtained;
       ii. the ophthalmic image is stored in the storage components;
       iii. the ophthalmic image is retrieved and classified by passage through the trained weighted-ensemble;
       iv. the image class such as disease state and stage is provided as output; and
       v. the image class can be transmitted over a network to a third party for storage, further interpretation, and/or appropriate action.

15. The method of claim 14 wherein the ophthalmic image is obtained by an integrated local device which captures the image of an eye or some of its parts in real time.

16. The method of claim 14 wherein the ophthalmic image is obtained by retrieval from a remote imaging system or database.

17. The method of claim 14 wherein some of the models in the ensemble are convolutional neural networks.

18. The method of claim 14 wherein some of the models in the ensemble are recurrent neural networks.

19. The method of claim 14 wherein the trained weighted-ensemble is trained as follows:
    a) a database of labeled ophthalmic images is split into training and test sets;
    b) each model in the ensemble is trained and tested;
    c) the models are ranked based on their performance on the test dataset; and
    d) a model weight is assigned to each model based on its performance rank.

20. The method of claim 19 wherein classification of an ophthalmic image is done as follows:
    a) the image is passed through each model, generating probabilistic class scores for each;
    b) using the model weights, a weighted-average of the probabilistic class scores is computed across models; and
    c) the weighted-average of class scores is used to classify the image.

* * * * *